(12) United States Patent
DeCarlo

(10) Patent No.: US 7,594,681 B2
(45) Date of Patent: Sep. 29, 2009

(54) FLUID LINE COUPLING

(75) Inventor: Arnold V. DeCarlo, Frederick, CO (US)

(73) Assignee: TYCO Healthcare Group LP, North Haven, CT (US)

( * ) Notice: Subject to any disclaimer, the term of this patent is extended or adjusted under 35 U.S.C. 154(b) by 147 days.

(21) Appl. No.: 11/880,022

(22) Filed: Jul. 19, 2007

(65) Prior Publication Data
US 2009/0021002 A1    Jan. 22, 2009

(51) Int. Cl.
*F16L 47/00* (2006.01)

(52) U.S. Cl. .................... 285/294.1; 285/417; 285/919

(58) Field of Classification Search ............. 285/290.1, 285/294.1, 417, 919, 295.1, 404
See application file for complete search history.

(56) References Cited

U.S. PATENT DOCUMENTS

| | | | | |
|---|---|---|---|---|
| 269,011 A * | 12/1882 | Clatworthy | ............... | 285/294.1 |
| 283,973 A * | 8/1883 | Converse | ................ | 285/294.1 |
| 3,473,833 A * | 10/1969 | Bremer | ................... | 285/285.1 |
| 3,561,795 A * | 2/1971 | Becher | ..................... | 285/294.1 |
| 3,796,057 A * | 3/1974 | Dougherty | ................... | 285/417 |
| 4,632,435 A | 12/1986 | Polyak | | |
| 5,150,922 A * | 9/1992 | Nakashiba et al. | .......... | 285/919 |
| 6,494,501 B2 | 12/2002 | Gotoh | | |
| 6,789,822 B1 * | 9/2004 | Metcalfe | ..................... | 285/404 |
| 6,857,670 B2 * | 2/2005 | Fritze | ..................... | 285/294.1 |
| 2005/0149010 A1 | 7/2005 | Turovskiy et al. | | |

* cited by examiner

*Primary Examiner*—David E Bochna

(57) ABSTRACT

A fluid line coupling is disclosed for connection with hollow tubing. The coupling includes a body portion having a passageway for fluid communication with the tubing. A first wall extends from the body portion radially surrounding the passageway, and a second wall radially surrounds the first wall forming a pocket between the walls. The second wall includes an aperture for fluid communication with the pocket. An open ended aperture may be included in a radial array of apertures. The first wall may include a tapered surface for securing the tubing. A third wall may radially surround the second wall forming a well for an adhesive for filling the aperture and pocket. A second set of walls may extend in an axially opposite direction from the first set. The coupling may be included in a connection assembly with hollow tubing comprising a PVC material providing fluid communication with a medical instrument.

14 Claims, 3 Drawing Sheets

FLUID LINE COUPLING

BACKGROUND

1. Technical Field

The present disclosure relates generally to an apparatus for connecting flexible tubing, piping and similar conduits. In particular, the disclosure relates to a fluid line coupling suitable for use in a medical device, which is capable of making a fluid-tight interconnection with a length of tubing or between lengths of tubing.

2. Background of Related Art

Plastic tubing, formed from materials such as polyvinyl chloride (PVC) or polyurethane, has a variety of uses and is particularly useful in the medical field. The flexibility and other qualities of such tubing, for example, makes it suitable for use in the delivery of fluids directly to and from patients, or for the conveyance of fluids to and from medical instruments. For many of these applications, it is necessary to use special couplers and fittings to interconnect two lengths of tubing to one another, to interconnect a length of tubing to a fluid source or an instrument, or to make any other required connection. The reliability of such couplings is particularly important for surgical equipment, the use of which provides little or no opportunity for repair in the event of a failure.

Tubing used in a cooling system for a medical device may present additional difficulties due to the relatively high pressures and temperatures which may be involved. One particular type of coupling for accommodating these difficulties incorporates an adhesive to bond and/or seal the end of a length of tubing inside a sleeve and also to fill all gaps between the tubing and the sleeve. The reliability of such a joint depends largely on the quality of the bond created.

Accordingly, a need exists for a fluid line coupling capable of creating a high quality adhesive bond for a fluid-tight connection to a length of hollow tubing.

SUMMARY

The present disclosure describes a fluid line coupling for connection to a length of hollow tubing. The coupling includes a body portion defining a longitudinal axis and including a fluid passageway therethrough. A first wall extends axially from at least one end of the body portion and at least partially around the fluid passageway. A second wall extends axially from the at least one end of the body portion and at least partially around the first wall. The second wall is spaced a radial distance from the first wall such that a pocket is formed between the first and second walls. At least one aperture is formed in the second wall such that the aperture is in fluid communication with the pocket.

The fluid line coupling may include at least one aperture formed in the second wall that is open ended, and the at least one aperture may include a radial array of apertures. The first wall of the fluid line coupling may include a tapered outer surface. The fluid line coupling may also include a third wall extending substantially axially from the at least one end of the body portion and at least partially around the second wall spaced a radial distance from the second wall such that a well is defined between the second and third walls. The fluid line coupling may provide an adhesive in the pocket and at least one aperture formed in the second wall. The at least one end of the body portion from which the first and second walls extend may include a first end and an axially opposed second end of the body portion such that at least two sets of walls extend from the body portion.

The present disclosure further describes a fluid line connection assembly including flexible hollow tubing, a coupling and an adhesive for bonding the flexible hollow tubing to the coupling. The coupling includes a body portion defining a passageway therethrough for fluid communication with the flexible hollow tubing, and inner and intermediate walls extending axially from an end of the body portion. The inner wall substantially surrounds the passageway, and the intermediate wall is substantially spaced from the inner wall such that a pocket is defined between the inner and intermediate walls. An aperture is formed in the intermediate wall in fluid communication with the pocket.

The flexible tubing of the fluid line connection assembly may comprise a PVC material. The body portion of the coupling may comprise a well radially surrounding the intermediate wall for containing a quantity of adhesive. The well of the body portion may include a radially enlarged opening for facilitating the injection of the adhesive into at least one of the well and pocket. The coupling may provide fluid communication between the flexible hollow tubing and a medical instrument. The body portion of the coupling may further comprise an outer wall extending axially from the at least one end of the body portion and substantially radially surrounding the well. The at least one end of the body portion may include two axially opposed ends of the body portion. The at least one aperture formed in the intermediate wall may be open ended.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF EMBODIMENTS

Figure 1:
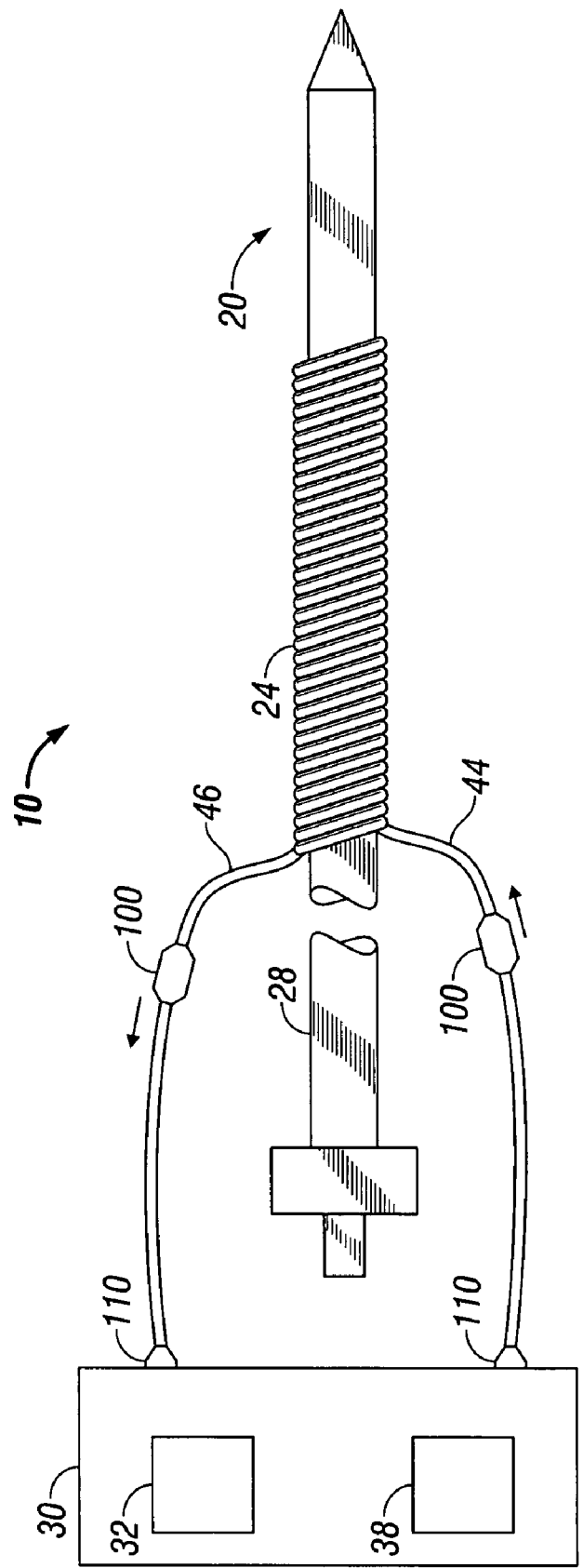
FIG. 1 is a schematic representation of a medical instrument system employing several fluid line couplings in accordance with the present disclosure.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Referring initially to FIG. 1, a medical/instrument system is generally depicted as 10. Medical/instrument system 10 includes a tissue ablation antenna 20 having a cooling coil 24 wrapped therearound and fluid line couplings 100, 110 of the present disclosure, for interconnecting cooling coil 24 to a cooling unit or system 30.

As seen in FIG. 1, tissue ablation antenna 20 includes a shaft 28 which may be cooled by the circulation of a suitable fluid such as water, saline, carbon dioxide, etc., through cooling coil 24. A cooling unit 30 may be fluidly connected to cooling coil 24. Cooling unit 30 may include a heat exchanger 32 for cooling the fluid, and a pump 38 to force the cool fluid into or through an inlet line 44 of coil 24, where the fluid is heated by antenna 20, and out of or through output line 46 of coil 24 that returns the fluid to cooling unit 30. Reference may be made to U.S. Patent Application Publication No. 2005/0149010, filed on Jul. 7, 2005 for a detailed description of various exemplary devices and methods for cooling ablation antennas and the like.

With continued reference to FIG. 1, fluid line couplings 100 may be used to provide fluid communication and/or interconnection between adjacent tubing in an end-to-end arrangement, and fluid couplings 110 may be used to provide fluid communication and/or interconnection between fluid tubing and a device. Other alternative configurations for fluid couplings, such as right angle elbows, T-connectors, reducers, and other standard configurations, are also envisioned by the present disclosure.

Figure 2:
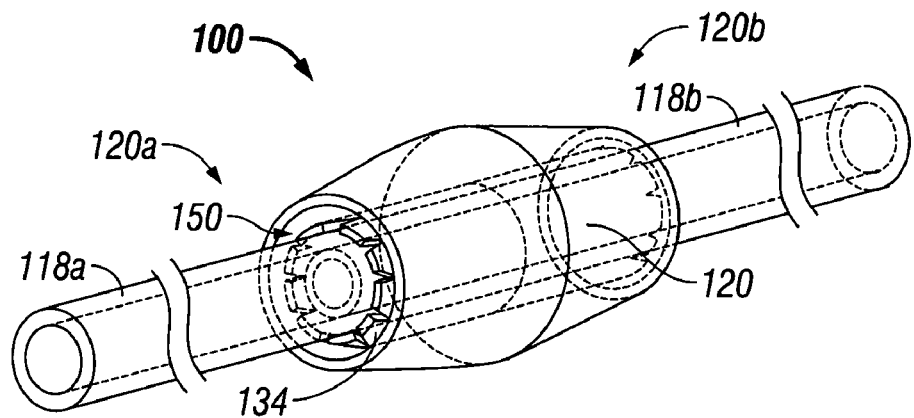
FIG. 2 is a perspective view of a fluid line coupling in accordance with an embodiment of the present disclosure, illustrating a tubing connector thereof.

Referring now to FIGS. 2-5, a fluid line coupling in accordance with the present disclosure is designated as 100. As seen in FIG. 2, fluid line coupling 100 includes two lengths of tubing 118a, 118b connected thereto, in an end-to-end configuration. Tubing 118a, 118b is a hollow conduit, which may be formed from a suitable flexible material (e.g. PVC or similar material).

Fluid line coupling 100 includes a body portion 120 defining a passage or lumen 126 therethrough such that the two sections of tubing 118a, 118b are in fluid communication with one another. Body portion 120 may be relatively rigid with respect to tubing 118a, 118b. Passage 126 of body portion 120 defines a longitudinal "X" axis.

Each end 120a, 120b of body portion 120 includes at least a first or inner wall 130 and a second or intermediate wall 134 extending substantially axially therefrom. First and second walls 130 and 134 define annular pocket 144 therebetween. First or inner wall 130 radially surrounds passageway 126, and second or intermediate wall 134 is radially spaced from first or inner wall by a dimension sufficient to define pocket 144 and to receive the end of tubing 118a, 118b within pocket 144.

Figure 3:
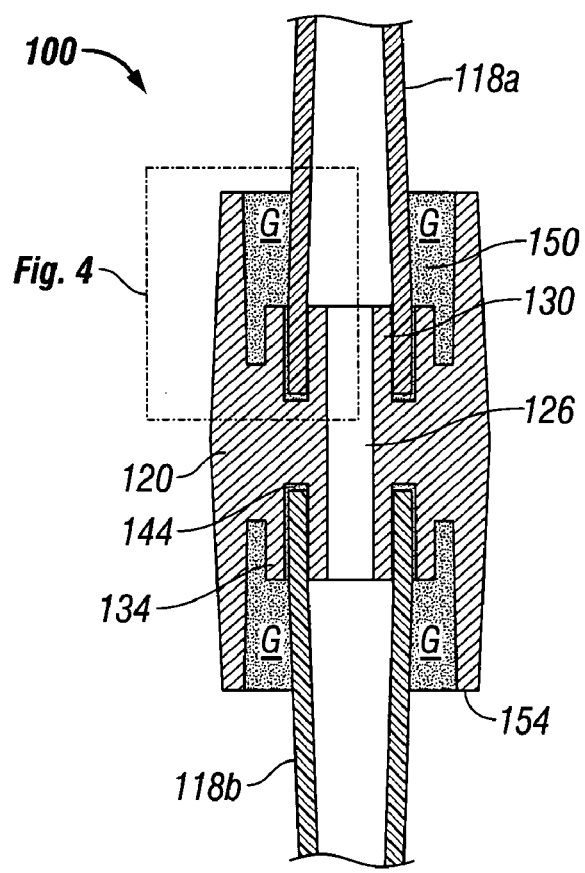
FIG. 3 is a longitudinal cross-sectional, view of the fluid line coupling of FIG. 2.

As seen in FIG. 3, first or inner wall 130 includes a taper or draft on an outer surface thereof adjacent to tubing 118a. The taper of first or inner wall 130 is sufficient to ensure a friction fit connection between tubing 118a and first or inner wall 130. An inner surface of second or intermediate wall 134 may be provided with a taper (not shown) to facilitate seating of tubing 118a within pocket 144.

Each end 120a, 120b of body portion 120 further includes an outer wall 154 spaced a radial distance away from second or intermediate wall 134 and defines a well 150 therebetween. Well 150 provides a reservoir for containing an adhesive or glue "G" within the respective end 120a, 120b of body portion 120. The adhesive or glue "G" is suitably selected to bond with the materials of construction of fluid line coupling 100 and tubing 118a, 118b, and to have a viscosity that allows adhesive or glue "G" to flow into any crevices which would otherwise prevent the establishment of a fluid-tight connection. Well 150 may be configured to be broader or wider at its opening in order to facilitate the application of adhesive or glue "G" in a sufficient quantity to effectively seal the connection between body portion 120 of fluid line coupling 100 and tubing 118a, 118b.

Figure 5:
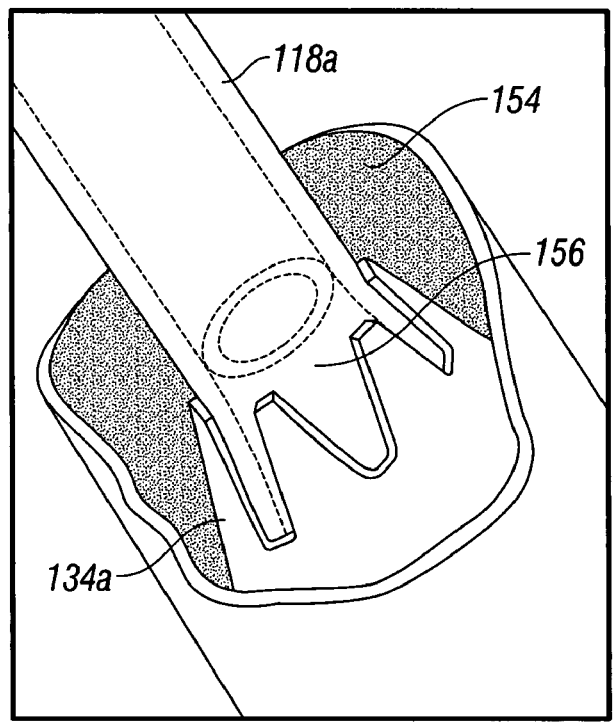
FIG. 5 is a perspective view, partially broken away, of the fluid line coupling of FIGS. 2-4.

As seen best in FIG. 5, second or intermediate wall 134 includes at least one radial aperture or recess 156 formed therein and extending into well 150. As seen in FIG. 5, any suitable number of apertures or recesses 156 may be provided radially around second or intermediate wall 134. Apertures or recesses 156 provide fluid communication between well 150 and an exterior surface of tubing 118a, 118b when tubing 118a, 118b is connected to fluid line coupling 100. Apertures or recesses 156 also function to increase a surface area on both second or intermediate wall 134 and tubing 118a, 118b available for bonding with adhesive or glue "G." It is contemplated that apertures or recesses 156 may take the form of open ended slots or channels (as shown), perforations, angled slots, etc., to provide the necessary fluid communication between well 150 and tubing 118a, 118b.

Figure 4:
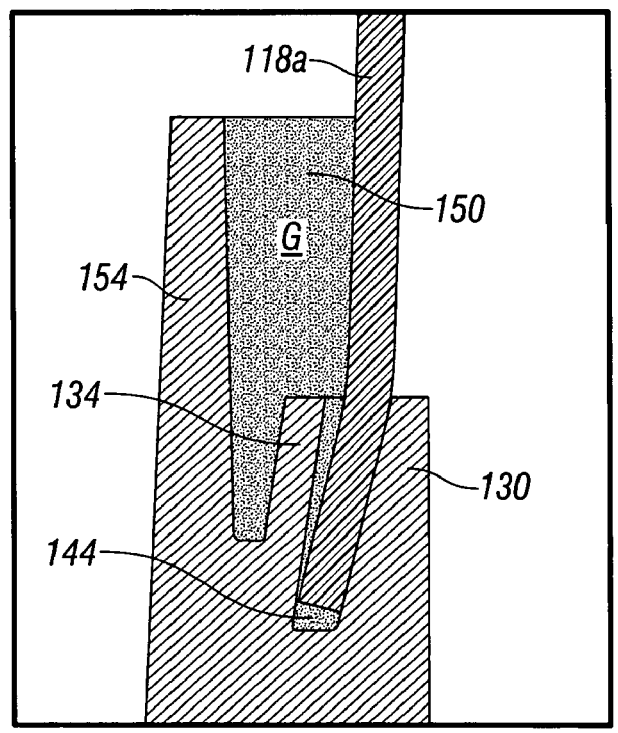
FIG. 4 is an enlarged view of the indicated area of detail of FIG. 3.

In use, to connect a length of tubing 118a, 118b to fluid line coupling 100, the end of a length of tubing 118a, 118b is inserted axially into fluid line coupling 100, between first or inner wall 130, and second or intermediate wall 134, such that the end of tubing 118a, 118b is inserted into pocket 144 and first or inner wall 130 is inserted into a lumen of tubing 118a, 118b. As seen in FIGS. 3 and 4, an inner circumferential surface of the tubing 118a, 118b engages first or inner wall 130, and an outer circumferential surface of tubing 118a, 118b engages an inner surface of second or intermediate wall 134 as tubing 118a, 118b is advanced into pocket 144. The taper or draft on first or inner wall 130 flares or radially expands the end of tubing 118a, 118b and wedges it into position as it approaches a bottom of the pocket 144. This creates a stable condition where the tubing is held in place to allow the well 150 to be filled with adhesive or glue "G."

The adhesive or glue "G" is injected into well 150 in an amount sufficient to flow into, and fill any crevices or potential leak paths between tubing 118a, 118b and fluid line coupling 100. Well 150 is broad around a mouth thereof to facilitate the application of an excess quantity of adhesive or glue "G" therein. Apertures or recesses 156 provide an increased surface area on both the second or intermediate wall and tubing 118a, 118b to which adhesive or glue "G" may bond. This feature ensures that any potential leak paths are filled with adhesive or glue "G," and that a bond between tubing 118a, 118b and fluid line coupling 100 is robust.

Once adhesive or glue "G" has set, the connection between tubing 118a, 118b and fluid line coupling 100 is substantially fluid-tight. In operation if a fluid pressure within passageway 126 of fluid line coupling 100 is increased, the tendency for tubing 118a, 118b to expand radially will be counteracted by a rigidity of second or intermediate wall 134, which will prevent any outward radial expansion of tubing 118a, 118b which might otherwise create a fluid leak path. Second or intermediate wall 134 provides a radially inwardly directed constant and/or uniform pressure on tubing 118a, 118b. Furthermore, first or inner and second or intermediate walls 130, 134 support tubing 118a, 118b and prevent any unintended movement of tubing 118a, 118b relative to fluid line coupling 100, caused by handling of medical/instrument system 10.

As mentioned above, other embodiments of a fluid line coupling are envisioned. For example, a fluid-line coupling 110, as depicted in FIG. 1, includes the structure necessary to connect a single length of tubing 118a or 118b to a device 30. Also, reducers are envisioned that will allow for two different diameters of tubing to be connected in an end-to-end configuration or in an angled configuration.

Although the foregoing disclosure has been described in some detail by way of illustration and example, for purposes of clarity or understanding, certain changes and modifications may be practiced within the scope of the appended claims.

What is claimed is:

1. A fluid line coupling for connection to a length of hollow tubing, the fluid line coupling comprising:

a body portion defining a fluid passageway therethrough and a longitudinal axis;

a first wall extending substantially axially from at least one end of the body portion and at least partially radially around the fluid passageway;

a second wall extending substantially axially from the at least one end of the body portion and at least partially around the first wall, wherein the second wall is spaced a radial distance from the first wall and defines a pocket therebetween, the second wall including at least one aperture formed therein and being in fluid communication with the pocket; and an adhesive provided in the pocket and in the at least one aperture formed in the second wall.

2. The fluid line coupling according to claim 1, wherein the at least one aperture is open ended.

3. The fluid line coupling according to claim 1, wherein the at least one aperture includes a radial array of apertures.

4. The fluid line coupling according to claim 1, wherein the first wall includes a tapered outer surface thereof for wedging the section of hollow tubing.

5. The fluid line coupling according to claim 1, wherein the at least one end of the body portion includes two axially opposed ends of the body portion.

6. A fluid line coupling for connection to a length of hollow tubing, the fluid line coupling comprising:

a body portion defining a fluid passageway therethrough and a longitudinal axis;

a first wall extending substantially axially from at least one end of the body portion and at least partially radially around the fluid passageway;

a second wall extending substantially axially from the at least one end of the body portion and at least partially around the first wall, wherein the second wall is spaced a radial distance from the first wall and defines a pocket therebetween, the second wall including at least one aperture formed therein and being in fluid communication with the pocket; and a third wall extending substantially axially from the at least one end of the body portion and at least partially around the second wall, wherein the third wall is spaced a radial distance from the second wall and defines a well therebetween.

7. A fluid line connection assembly comprising:
flexible hollow tubing;
a coupling including:

a body portion defining a passageway therethrough for fluid communication with the flexible hollow tubing; and an inner and an intermediate wall extending axially from at least one end of the body portion and substantially surrounding the passageway, the inner and intermediate wall being spaced from one another to define a pocket therebetween for receiving an end of the flexible hollow tubing, the intermediate wall including at least one aperture formed therein and in fluid communication with the pocket; and an adhesive provided in the pocket and in each aperture formed in the intermediate wall for bonding the flexible hollow tubing to the coupling.

8. The fluid line connection assembly according to claim 7, wherein the flexible hollow tubing comprises a PVC material.

9. The fluid line connection assembly according to claim 7, wherein the body portion of the coupling further comprises a well radially surrounding the intermediate wall for containing a quantity of adhesive.

10. The fluid line connection assembly according to claim 9, wherein the well of the body portion includes a radially enlarged opening for facilitating the injection of the adhesive into at least one of the well and pocket.

11. The fluid line connection assembly according to claim 7, wherein the coupling provides fluid communication between the flexible hollow tubing and a medical instrument.

12. The fluid line connection assembly according to claim 7, wherein the coupling further comprises an outer wall extending axially from the at least one end of the body portion and substantially radially surrounding the well.

13. The fluid line connection assembly according to claim 7, wherein the at least one end of the body portion includes two axially opposed ends of the body portion.

14. The fluid line connection assembly according to claim 7, wherein the at least one aperture formed in the intermediate wall is open ended.

\* \* \* \* \*